United States Patent [19]
Heyneker

[11] Patent Number: 6,057,100
[45] Date of Patent: May 2, 2000

[54] OLIGONUCLEOTIDE ARRAYS

[75] Inventor: Herbert L. Heyneker, Hillsborough, Calif.

[73] Assignee: EOS Biotechnology, Inc., South San Francisco, Calif.

[21] Appl. No.: 08/870,514

[22] Filed: Jun. 6, 1997

Related U.S. Application Data

[60] Provisional application No. 60/018,954, Jun. 7, 1996.

[51] Int. Cl.[7] ............................. C12Q 1/68; C07H 21/02
[52] U.S. Cl. ............................................. 435/6; 536/23.1
[58] Field of Search ....................... 435/6, 91.2; 935/77, 935/78; 536/2

[56] References Cited

U.S. PATENT DOCUMENTS

| | | | |
|---|---|---|---|
| 3,551,295 | 12/1970 | Dyer | 195/103.5 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,217,492 | 6/1993 | Guire et al. | 623/11 |
| 5,258,041 | 11/1993 | Guire et al. | 623/66 |
| 5,263,992 | 11/1993 | Guire | 623/66 |
| 5,318,679 | 6/1994 | Nishioka | 204/157.88 |
| 5,427,779 | 6/1995 | Elsner et al. | 424/78.17 |
| 5,449,754 | 9/1995 | Nishioka | 530/334 |
| 5,510,270 | 4/1996 | Fodor et al. | 436/18 S |
| 5,545,531 | 8/1996 | Rava et al. | 435/6 |
| 5,700,637 | 12/1997 | Southern | 435/6 |

FOREIGN PATENT DOCUMENTS

| | | |
|---|---|---|
| 0 445 915 | 9/1991 | European Pat. Off. . |
| 95/11748 | 5/1995 | WIPO . |

OTHER PUBLICATIONS

Schena et al., "Quantitative Monitoring of Gene Expression Patterns with a Complementary DNA Microarray," *Science*, 270:457–470 (1995).

Amos et al.,"Surface Modification of Polymers by Photochemical Immobilization—A General Method," The 17th Annual Meeting of the Society for Biomaterials, Scottsdale, Arizona (May 1–5, 1991).

Breidenthal et al., "Dispensing Options for Immunoassays," *IVD Technology*, 2(5):40–45 (1996).

"PhotoLink Surface Modification Guide," BSI Corporation, Eden Prairie: Minnesota, pp. 1–8 (1994).

Jacobs et al, (Diag. Microbiol. Infec. Dises. 15(5):475–8, 1992.

*Primary Examiner*—Eggerton A. Campbell
*Attorney, Agent, or Firm*—Flehr Hohbach Test Albritton & Herbert LLP; David J. Brezner, Esq.; Robin M. Silva, Esq.

[57] ABSTRACT

The invention relates to novel oligonucleotide arrays.

19 Claims, 3 Drawing Sheets

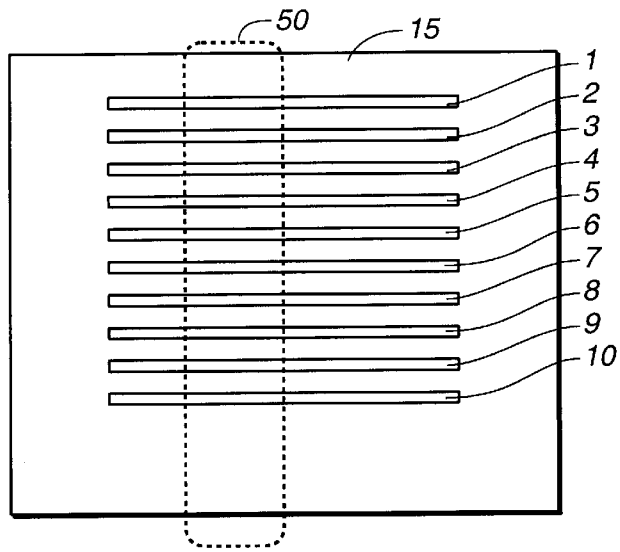
FIG._1A
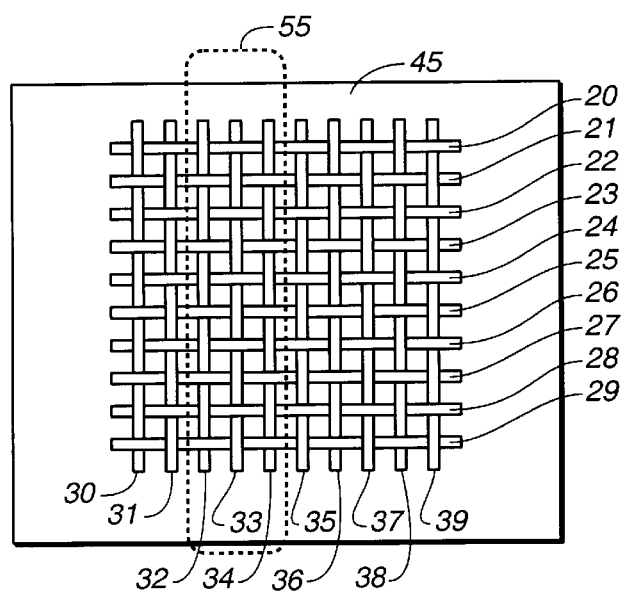
FIG._1B
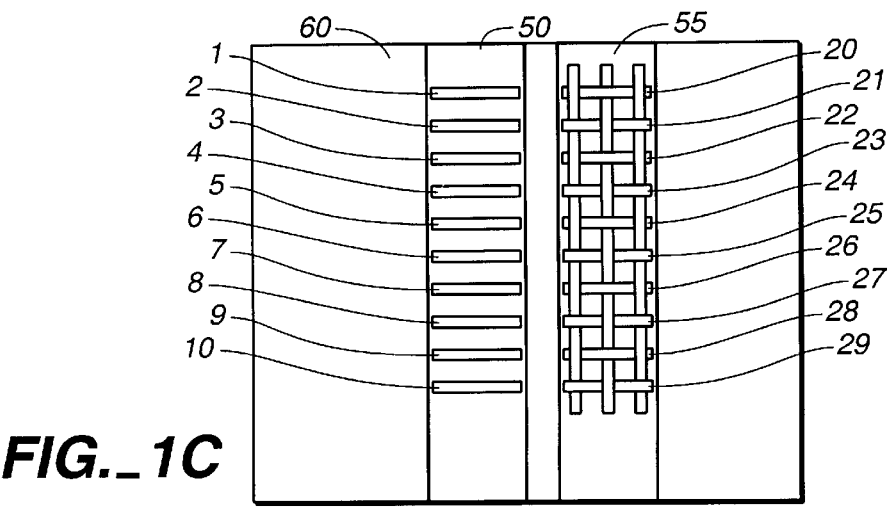
FIG._1C

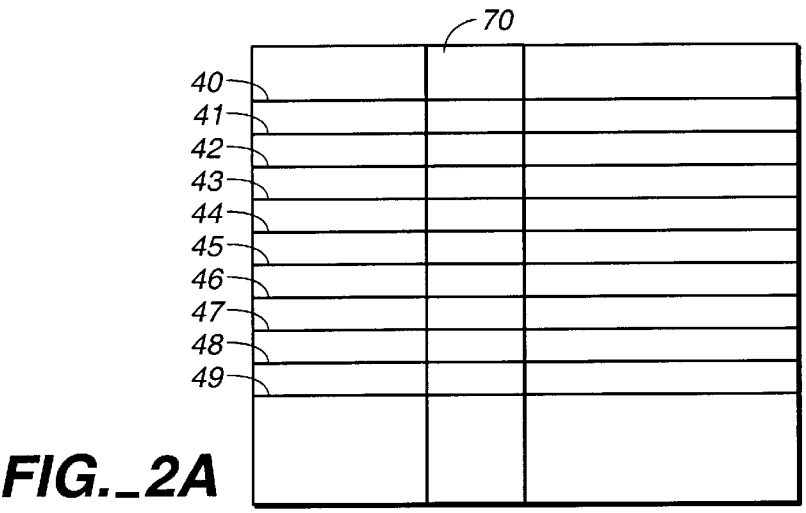
FIG._2A
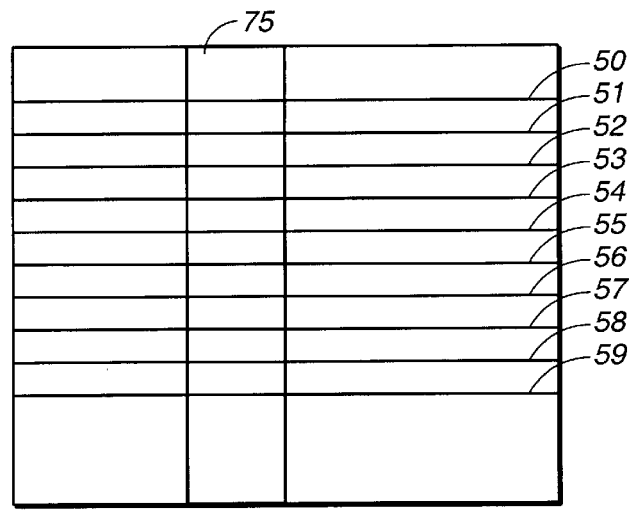
FIG._2B
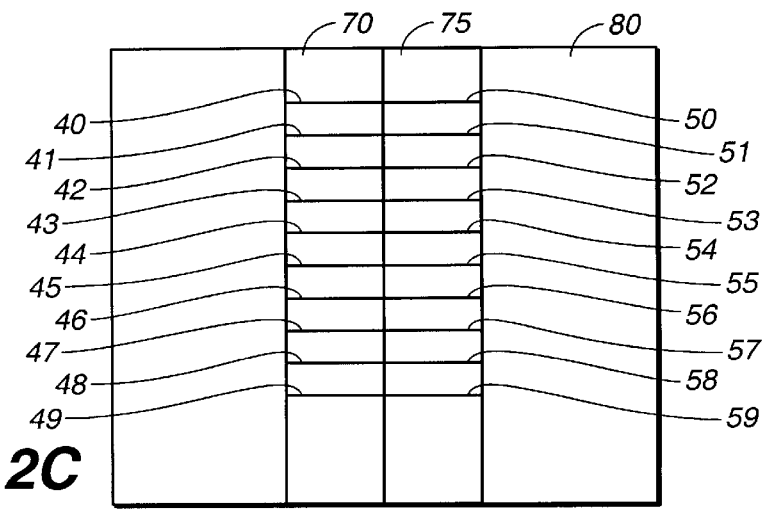
FIG._2C

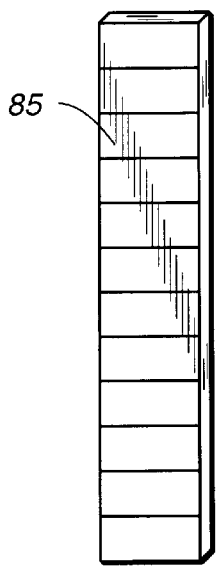
FIG._3A
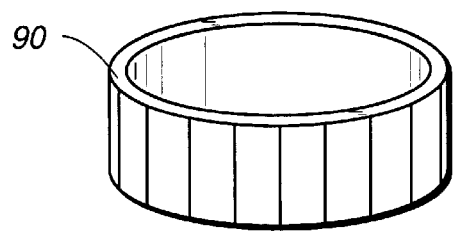
FIG._3B
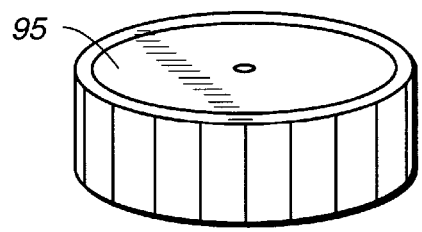
FIG._3C
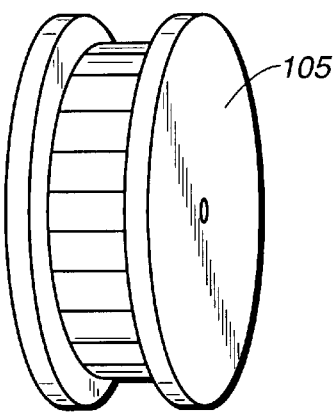
FIG._3E
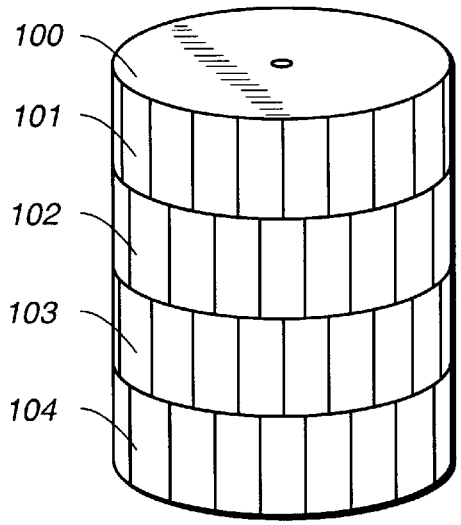
FIG._3D

OLIGONUCLEOTIDE ARRAYS

This application claims benfit of Provisional Application No. 60/018,954 filed jun. 7, 1996.

FIELD OF THE INVENTION

The invention relates to novel oligonucleotide arrays.

BACKGROUND OF THE INVENTION

The use of oligonucleotide arrays in nucleic acid detection and sequencing, and in particular for clinical diagnosis, is a rapidly growing field. Generally, an oligonucleotide array is comprised of a number of individual oligonucleotides linked to a solid support in a regular pattern, each one in a different area, so that the location of each oligonucleotide is known. After generation of the array, samples containing the target sequences are exposed to the array, hybridized to the complementing oligonucleotides bound in the array, and the hybridized sequences are detected using a wide variety of methods, most commonly radioactive or fluorescent labels.

Currently there are a variety of technologies available to generate oligonucleotide arrays. Generally, the arrays are prepared by synthesizing all of the oligonucleotides simultaneously on the solid support, using solid-phase synthesis combined with some type of masking or chemical protection to allow for the selective addition of the nucleotides at any particular position. A preferred method uses photolithographic techniques. Alternatively, micro-dispensing of oligonucleotides onto functionalized solid supports is done.

However, there are a number of problems associated with this type of synthesis. In particular, when every addition of every nucleotide is a separate reaction on a single solid support, the reproducibility and yield may vary widely as between different locations on the support, as well as between supports. Micro-dispensing can also show variability. Additionally, the equipment and materials need to generate the arrays can be quite costly.

Accordingly, it is an object of the invention to provide oligonucleotide arrays which can be easily generated and are highly reproducible, and methods of using such arrays.

SUMMARY OF THE INVENTION

In accordance with the objects outlined above, the present invention provides oligonucleotide arrays comprising a solid support comprising a plurality of different oligonucleotide pools. Each oligonucleotide pool is arranged in a distinct linear row to form an immobilized oligonucleotide stripe, wherein the length of each stripe is greater than its width.

In a further aspect, the invention provides composite arrays comprising at least one strip of a first array and at least one strip of a second array.

In an additional aspect, the invention provides methods of making an oligonucleotide arrays comprising activating a support surface and adding oligonucleotide pools to the activated support surface to form oligonucleotide stripes.

Further provided are methods of detecting the presence or absence of a target sequence in a sample. The methods comprise contacting the sample with a array under conditions that permit hybridization of the target sequence, if present, to an oligonucleotide covalently attached to the array. The resulting hybridization complex is then detected as an indicator of the presence or absence of the target sequence.

BRIEF DESCRIPTION OF THE DRAWINGS

FIGS. 1A–1C depicts an array of the invention utilizing 10 fibers, labelled 1 through 10, and backing (15). FIG. 1B depicts a woven array with 10 weft fibers (20–29) and 10 warp fibers (30–39), and backing (45). FIG. 1C depicts the addition of two strips (50 and 55) forming a composite array (60).

FIGS. 2A–2C depicts a single support surface array, utilizing 10 oligonucleotides, labelled 40–49. FIG. 2B depicts a second single support surface array, utilizing 10 oligonucleotides, labelled 50–59. FIG. 2C depicts a composite array (65) of two strips (70 and 75) and a backing (80).

FIGS. 3A–3D depicts a strip of an array of the invention (85) which can be circularized in a number of ways. FIG. 3B depicts the strip in one possible circular form (90), and FIG. 3C depicts an alternative circular form, a disk form. FIG. 3D depicts a composite array (100) comprising four different disk arrays (101, 102, 103 and 104). FIG. 3E depicts a circular array in a housing or casing that will protect the surface, i.e. the oligonucleotide stripes or fibers.

DETAILED DESCRIPTION OF THE INVENTION

The present invention is directed to oligonucleotide arrays, and methods of making and using such arrays. As outlined above, current oligonucleotide arrays are made wherein each solid support has a number of different oligonucleotides attached, thus requiring that a number of different synthetic or attachment reactions occur on each solid support, thus causing variability both on any single support as well as between identical but separate supports. Known techniques generally build the oligonucleotides one nucleotide at a time on the surface of the support, thus requiring numerous steps with yield losses at each step. Furthermore, the length of the oligonucleotides that can be generated in this way is generally finite, and thus can require a greater number of shorter oligonucleotides for detection of target sequences. Alternatively, techniques such as microdispensing of oligonucleotides onto functionalized supports also can show variability.

The present invention circumvents these problems by generating large arrays using presynthesized oligonucleotides laid down in linear rows to form an array, which then can be divided or cut into strips, to form a number of smaller, uniform arrays. Strips from different arrays can be combined to form more complex composite arrays. In this way, both the efficiency of oligonucleotide attachment (or synthesis) is improved, and there is a significant increase in reproducibility of the arrays.

One advantage of the present invention is that the oligonucleotides each form an oligonucleotide stripe that is longer than it is wide; that is, when hybridization to a target sequence occurs, a stripe of hybridization occurs. This significantly increases the ability to distinguishing over non-specific hybridization and background effects when detection is via visualization, such as through the use of radioisotope detection. When other types of detection such as fluorescence is used, the length of the stripe allows repeated detection reactions to be made, with or without slight variations in the position along the length of the stripe. Averaging of the data points allows the minimization of false positives or position dependent noise such as dust, microdebris, etc.

Thus, the present invention provides oligonucleotide arrays comprising a solid support comprising a plurality of different oligonucleotide pools. By "plurality" herein is meant at least two different oligonucleotide species, with from about 10 to 1000 being preferred, and from about 50 to 500 being particularly preferred and from about 100–200 being especially preferred, although smaller or larger number of different oligonucleotide species may be used as well. As will be appreciated by those in the art, the number of oligonucleotides per array will depend in part on the size and composition of the array, as well as the end use of the array. Thus, for certain diagnostic arrays, only a few different oligonucleotide probes may be required; other uses such as cDNA analysis may require more oligonucleotide probes to collect the desired information.

The composition of the solid support may be anything to which oligonucleotides may be attached, preferably covalently, and will also depend on the method of attachment. Preferably, the solid support is substantially nonporous; that is, the oligonucleotides are attached predominantly at the surface of the solid support.

Accordingly, suitable solid supports include, but are not limited to, those made of plastics, resins, polysaccharides, silica or silica-based materials, functionalized glass, modified silicon, carbon, metals, inorganic glasses, membranes, nylon, natural fibers such as silk, wool and cotton, and polymers. In some embodiments, the material comprising the solid support has reactive groups such as carboxy, amino, hydroxy, etc., which are used for attachment of the oligonucleotides. Alternatively, the oligonucleotides are attached without the use of such functional groups, as is more fully described below. Polymers are preferred, and suitable polymers include, but are not limited to, polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate and polymethylpentene. Preferred polymers include those outlined in U.S. Pat. No. 5,427,779, hereby expressly incorporated by reference.

The solid support has covalently attached oligonucleotides. By "oligonucleotide" or "nucleic acid" or grammatical equivalents herein is meant at least two nucleotides covalently linked together. A nucleic acid of the present invention will generally contain phosphodiester bonds, although in some cases, as outlined below, a nucleic acid may have an analogous backbone, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, phosphoramidate, O-methylphophoroamidite linkages (see Eckstein, Oligonucleotides and Analogues: A Practical Approach, Oxford University Press), peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)) or morpholino-type backbones. These modifications of the ribose-phosphate backbone may be done to increase the stability and half-life of such molecules in physiological environments, or to increase the stability of the hybridization complexes (duplexes). Generally, the attached oligonucleotides are single stranded. The oligonucleotide may be DNA, both genomic and cDNA, RNA or a hybrid, where the oligonucleotide contains any combination of deoxyribo- and ribo-nucleotides, and any combination of uracil, adenine, thymine, cytosine and guanine, as well as other bases such as inosine, xanthine and hypoxanthine.

The length of the oligonucleotide, i.e. the number of nucleotides, can vary widely, as will be appreciated by those in the art. Generally, oligonucleotides of at least 6 to 8 bases are preferred, with oligonucleotides ranging from about 10 to 500 being preferred, with from about 20 to 200 being particularly preferred, and 40 to 100 being especially preferred. Longer oligonucleotides are preferred, since higher stringency hybridization and wash conditions may be used, which decreases or eliminates non-specific hybridization. However, shorter oligonucleotides may be used if the array uses levels of redundancy to control the background, or utilizes more stable duplexes.

The covalent attachment of the oligonucleotides to the solid support is described below. As will be appreciated by those in the art, either the 5' or 3' terminus may be attached to the support.

The arrays of the invention comprise at least two different covalently attached oligonucleotide species, with more than two being preferred. By "different" oligonucleotide herein is meant an oligonucleotide that has a nucleotide sequence that differs in at least one position from the sequence of a second oligonucleotide; that is, at least a single base is different. As will be appreciated by those in the art, arrays can be made wherein not every stripe contains an oligonucleotide. That is, when the solid support comprises a number of different support surfaces, such as fibers, as is generally outlined below, not every fiber must contain an oligonucleotide. For example, "spacer" fibers (or rows, when a single support surface is used) may be used to help alignment or detection. In a preferred embodiment, every row or fiber has a covalently attached oligonucleotide. In this embodiment, some rows or fibers may contain the same oligonucleotide, or all the oligonucleotides may be different. Thus, for example, it may be desirable in some applications to have rows or fibers containing either positive or negative controls, evenly spaced throughout the array, i.e. every nth fiber or row is a control. Similarly, any level of redundancy may be built into the array; that is, different fibers or rows containing identical oligonucleotides may be used.

The space between the oligonucleotide stripes can vary widely, although generally is kept to a minimum in the interests of miniaturization. The space will depend on the methods used to generate the array; for example, for woven arrays utilizing fibers, the methodology utilized for weaving may determine the space between the fibers.

Each oligonucleotide pool or species is arranged in a distinct linear row to form an immobilized oligonucleotide stripe. By "distinct" herein is meant that each row is separated by some physical distance. By "immobilized" herein is meant that the oligonucleotide is attached to the support surface, preferably covalently, as is outlined herein. By "stripe" herein is meant a conformation of the oligonucleotide species that is longer than it is wide. When the array comprises a number of different support surfaces, such as outlined above for fibers, each stripe is a different fiber.

In a preferred embodiment, as is more fully described below, the solid support comprises a single support surface. That is, a plurality of different oligonucleotide pools are attached to a single support surface, in distinct linear rows, forming oligonucleotide stripes. In a preferred embodiment, the linear rows or stripes are parallel to each other; that is, they form stripes as shown in FIG. 2. However, any conformation of stripes may be used as well. In this embodiment, there are preferably at least about 1 stripe per millimeter, with at least about 2 stripes per millimeter being preferred, and at least about 3 stripes per millimeter being particularly preferred, although arrays utilizing from 3 to 10 stripes, or higher, per millimeter may also be generated, depending on the methods used to lay down the oligonucleotides.

In a preferred embodiment, the solid support comprises a plurality of separate support surfaces that are combined to form a single array. In this embodiment, each support surface can be considered a fiber. Thus, the array comprises a number of fibers, each of which can contain a different oligonucleotide. That is, only one oligonucleotide species is attached to each fiber, and the fibers are then combined to form the array.

By "fiber" herein is meant an elongate strand. Preferably the fiber is flexible; that is, it can be manipulated without breaking. The fiber may have any shape or cross-section. The fibers may comprise, for example, long slender strips of a solid support that have been cut off from a sheet of solid support. Alternatively, and preferably, the fibers have a substantially circular cross section, and are typically thread-like. Fibers are generally made of the same materials outlined above for solid supports, and each solid support may comprise fibers with the same or different compositions.

The fibers are associated into arrays in a number of ways, as will be appreciated by those in the art. In one embodiment, the fibers are aligned in a side-by-side manner as depicted in FIG. 1A, forming alignment fiber arrays. FIG. 1A depicts an array containing 10 fibers, although as will be appreciated by those in the art, any number of fibers can be used. Thus the fibers comprising the linear rows of the oligonucleotides, form parallel oligonucleotide stripes.

The fibers of the arrays of the invention may be held together in a number of ways. For example, the fibers may be held together via attachment to a backing or support. This is particularly preferred when the fibers are not physically interconnected, as is generally depicted in FIG. 1A. For example, adhesives may be used to hold the fibers to a backing or support, such as a thin sheet of plastic or polymeric material. In a preferred embodiment, the adhesive and backing are optically transparent, such that hybridization detection may be done through the backing. In a preferred embodiment, the backing comprises the same material as the fiber; alternatively, any thin films or sheets may be used. Suitable adhesives are known in the art, and will resist high temperatures and aqueous conditions. Alternatively, the fibers may be attached to a backing or support using clips or holders. In an additional embodiment, for example when the fibers and backing comprise plastics or polymers that melt, the fibers are attached to the backing via heat treatment at the ends. The fibers, i.e. the separate support surfaces, plus the means to hold them together, together form the solid support.

In a preferred embodiment, the fibers are woven together, as is generally depicted in FIG. 1B, to form woven fiber arrays. Thus, the array further comprises at least a third and a fourth fiber which are interwoven with the first and second fibers. In this embodiment, either or both of the weft (also sometimes referred to as the woof) and warp fibers contains covalently attached oligonucleotides. In a preferred embodiment, only the weft fibers contain oligonucleotides, as the strip arrays are generally cut between the warp fibers. However, the positional description of warp and weft may be arbitrary; what is important is that at least the fibers that span the width of the array or strip contain the oligonucleotides, rather than those that span the length. However, it is possible that in some embodiments only the warp fibers contain the oligonucleotides. In an additional embodiment, both the warp and the weft fibers contain oligonucleotides. Again, it is preferred that there are more than two weft fibers and more than two warp fibers, to generate larger woven fiber arrays.

In a preferred embodiment, arrays of the present invention are made and then sectioned into strips. A "strip" or "test strip" for the purposes of the invention is a section or piece of the array which contains at least a portion of every oligonucleotide-bearing stripe. Generally the strip is significantly longer than it is wide, although other configurations are possible. Preferred strips are from about 0.5 mm to 5 mm wide, with from about 1 to 5 mm being preferred.

In a preferred embodiment, the strip array is in circular form, as is generally depicted in FIG. 3. That is, the two ends of the array are attached, for example on the edge of a cylinder or disk (FIG. 3C), or forming a ring (FIG. 3B), to facilitate handling. Alternatively, the ends of the strip may not be in actual physical contact. The circular arrays may be associated to form composite arrays (100), for example by sliding the rings onto a cylinder, or associating the disks as depicted in FIG. 3D. The disks may have a hole or opening to facilitate attachment or handling. In addition, individual strip arrays or composite arrays may be housed in a casing that protects the surface and stripes of the array, as is schematically depicted in FIG. 3E.

One advantage of this circular-type conformation is that it can facilitate sample handling and hybridization, as well as detection. Thus for example the disks or rings may be rotated through a solution of the test sample; this agitation can increase the kinetics of hybridization. In addition, another advantage of the disk-type conformation is that detection can be done using a minimum of hardware. For example, when fluorescent labels are used to detect the target sequences, a single laser source, coupled with rotation of the array, can be used for detection, using technology similar to "bar code" readers.

In a preferred embodiment, the strips of different arrays are then placed adjacently together to form composite or combination arrays. A "composite" or "combination array" or grammatical equivalents is an array containing at least two strips from different arrays, as is generally depicted in FIG. 1C for a fiber array; the same types of composite arrays can be made from single support surface arrays, as is shown in FIG. 2C. That is, one strip is from a first fiber array, and another is from a second fiber array. The second fiber array has at least one covalently attached oligonucleotide that is not present in said first array, i.e. the arrays are different.

The composite arrays may be made solely of alignment arrays, solely of woven arrays, or a combination of different types. FIG. 1C depicts a composite array that has one alignment array (50) and one woven array (55); composite arrays can be made using any combination.

The width and number of strips in a composite array can vary, depending on the size of the fibers, the number of fibers, the number of target sequences for which testing is occurring, etc. Generally, composite arrays comprise at least two strips. As will be appreciated by those in the art, the composite arrays may comprise any number of strips, and may range from 2 to 1000, with from 5–100 being particularly preferred.

The strips of arrays in a composite array are generally adjacent to one another, such that the composite array is of a minimal size. However, there may be small spaces between the strips for facilitating or optimizing detection. Additionally, as for the fibers within an array, the strips of a composite array may be attached or stuck to a backing or support to facilitate handling.

As will be appreciated by those in the art, the method of making the oligonucleotide arrays of the present invention may vary. In a preferred embodiment, oligonucleotides are synthesized using traditional and well-known methods and then attached to the support surface. Alternatively, the oligonucleotides may be synthesized on the surface, as is known in the art. Preferred methods are outlined herein and are known in the art.

In a preferred embodiment, the oligonucleotides are synthesized as is known in the art, and then attached to the surface. In a preferred embodiment, the composition of the surface and the method of attachment is as described in U.S. Pat. Nos. 5,427,779; 4,973,493; 4,979,959; 5,002,582; 5,217,492; 5,258,041 and 5,263,992, and references cited therein, all of which are hereby expressly incorporated by reference. Briefly, coupling can proceed in one of two ways: a) the oligonucleotide is derivatized with a photoreactive group, followed by attachment to the surface; or b) the surface is first treated with a photoreactive group, followed by application of the oligonucleotide. Preferably, the activating agent is N-oxy-succinimide, which is put on the surface first, followed by attachment of a N-terminal amino-modified oligonucleotide, as is generally described in Amos et al., Surface Modification of Polymers by Photochemical Immobilization, The 17th Annual Meeting of the Society of Biomaterials, May 1991, Scottsdale AZ, hereby expressly incorporated by reference. Thus, for example, a suitable protocol involves the use of binding buffer containing 50 mM NaPhosphate pH 8.3, 15% $Na_2SO_4$ and 1 mm EDTA, with the addition of 0.1–10 pMole/µl of amino-terminally modified oligonucleotide. The sample is incubated for some time, from 1 second to about 45 minutes at 37° C., followed by washing (generally using 0.4 N NaOH/0.25% Tween-20), followed by blocking of remaining active sites with 1 mg/ml of BSA in PBS, followed by washing in PBS.

The methods allow the use of a large excess of an oligonucleotide, preferably under saturating conditions; thus, the uniformity along the stripe is very high.

In a preferred embodiment, the oligonucleotides are covalently attached to the support surface, using the techniques described herein. In an additional embodiment, the attachment may be very strong, yet non-covalent. For example, biotinylated oligonucleotides can be made, which bind to surfaces covalently coated with streptavidin, resulting in attachment.

In a preferred embodiment, a single support surface is used. In this embodiment, the oligonucleotides may be added to the surface in a variety of ways. In one embodiment, the entire surface is activated, followed by application of the oligonucleotide pools in linear rows, as outlined below, to form immobilized oligonucleotide stripes, with the appropriate blocking of the excess sites on the surface using known blocking agents such as bovine serum albumin. Alternatively, the activation agent may be applied in linear rows, followed by oligonucleotide attachment.

In this embodiment, the oligonucleotides may be applied to the surface in a number of ways. What is important is that the method of application results in a substantially uniform stripe. This may be done in several ways. In a preferred embodiment, the line is applied using ink jet technology, for example using a piezoelectric pump. In a preferred embodiment, the line is drawn, using for example a pen with a fine tip filled with the oligonucleotide solution. In one embodiment, the stripe is made using a series of dots for example using a plotter pen; that is, the repeated application of dots, separated by various distances, will result in a substantially uniform line. In addition, lines may be etched or scored into the surface to form uniform microtroughs, followed by filling of the microtrough with solution, for example using known microfluidic technologies. What is important is that the stripe be as uniform as possible.

When a number of support surfaces are used, the oligonucleotides are either synthesized or attached to a sheet of solid support, and then the sheet is cut or separated into fibers, i.e. thin strands. Alternatively, the oligonucleotides are synthesized or attached to individual fibers. When the oligonucleotides are synthesized on the fibers directly, a variety of known techniques may be used.

In this embodiment, once the oligonucleotides are attached to the fibers, the fibers are arranged to form arrays as is disclosed herein. As is outlined above, a preferred embodiment generates large arrays which are then sectioned into smaller strips which can be associated together to form composite arrays.

Once made, the arrays and composite arrays of the invention are used as will be appreciated by those in the art. Oligonucleotide arrays have a variety of uses, including the detection of target sequences, sequencing by hybridization, and other known applications (see for example Chetverin et al., Bio/Technology, Vol. 12, November 1994, pp1034–1099, (1994)).

In a preferred embodiment, the arrays are used to detect target sequences. The term "target sequence" or grammatical equivalents herein means a nucleic acid sequence on a single strand of nucleic acid. In some embodiments, a double stranded sequence can be a target sequence, when triplex formation with the probe sequence is done. The target sequence may be a portion of a gene, a regulatory sequence, genomic DNA, cDNA, mRNA, or others. It may be any length, with the understanding that longer sequences are more specific. As is outlined herein, oligonucleotides are made to hybridize to target sequences to determine the presence, absence, or relative amounts of the target sequence in a sample. Generally speaking, this term will be understood by those skilled in the art. The oligonucleotides of the present invention are designed to be complementary to the target sequence, such that hybridization of the target sequence and at least one oligonucleotide bound to the arrays of the present invention occurs.

In a preferred embodiment, the arrays are used in genetic diagnosis. For example, arrays can be made using the techniques disclosed herein to detect target sequences such as the gene for nonpolyposis colon cancer, the BRCA1 breast cancer gene, P53, which is a gene associated with a variety of cancers, and the Apo E4 gene that indicates a greater risk of Alzheimer's disease, allowing for easy presymptomatic screening of patients. Arrays can be made comprising all the known mutations of the cystic fibrosis gene.

In an additional embodiment, viral and bacterial detection is done using the arrays of the invention. In this embodiment, the oligonucleotides of the arrays are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial detection of tuberculosis and other bacterial infections may also be done.

In a preferred embodiment, the nucleic acids of the invention find use as probes for toxic bacteria in the screening of water and food samples. For example, samples may be treated to lyse the bacteria to release its nucleic acid, and then oligonucleotides designed to recognize bacterial strains, including, but not limited to, such pathogenic strains as, Salmonella, Campylobacter, *Vibrio cholerae*, enterotoxic strains of *E. coli*, and Legionnaire's disease bacteria. Similarly, bioremediation strategies may be evaluated using the arrays of the invention.

Similarly, arrays may be generated containing oligonucleotides designed to hybridize to mRNA sequences and used in differential display screening of different tissues, or for DNA indexing.

As is outlined herein, the arrays of the invention containing the oligonucleotides are contacted with a sample containing the target sequences under conditions which allow hybridization to occur. Generally, the samples are treated as is known in the art, including any sample preparation such as purification or amplification, followed by labeling of the target sequences, as is known in the art, using radioisotopes, or fluorescent or electrochemiluminescent compounds. In addition, in some embodiments, it may be desirable to chemically cross-link the two strands of the hybridization complex. The arrays containing the resulting hybridization complexes are then washed under a variety of stringency conditions ranging from low to high stringency, depending on the length and composition of the oligonucleotides. Detection of the hybridization complex proceeds as is known in the art.

In addition, the arrays of the invention may be formulated into kits containing the arrays and any number of reagents, such as PCR amplification reagents, labelling reagents, etc.

All references cited herein are incorporated by reference.

I claim:

1. An oligonucleotide array comprising a solid support comprising a plurality of different oligonucleotide pools, each oligonucleotide pool arranged in a distinct linear row to form an immobilized oligonucleotide stripe, wherein the length of each stripe is greater than its width.

2. An array according to claim 1 wherein said pools are covalently attached.

3. An array according to claim 1 wherein said solid support is plastic.

4. An array according to claim 1 wherein each of said rows are parallel to the other rows.

5. An oligonucleotide array according to claim 1 wherein said solid support is a single support surface.

6. An oligonucleotide array according to claim 1 wherein said stripes are laid down at a density of at least one per millimeter.

7. An oligonucleotide array according to claim 1 wherein said stripes are laid down at a density of at least two per millimeter.

8. An oligonucleotide array according to claim 1 wherein said stripes are laid down at a density of at least three per millimeter.

9. An oligonucleotide array according to claim 1 wherein said solid support comprises a plurality of support surfaces.

10. An oligonucleotide array according to claim 9 wherein each of said oligonucleotide pools is attached to a different support surface.

11. An array according to claim 10, wherein said array is in woven form.

12. An array according to claim 10, wherein said array is in alignment form.

13. An array according to claim 1, wherein said array is in circular form.

14. A composite array comprising at least one strip of a first array according to claim 1 and at least one strip of a second array according to claim 1, wherein at least one covalently attached oligonucleotide of the second array is not present in said first array, wherein said strips are adjacent.

15. A method of making an oligonucleotide array according to claim 5 or 9 comprising:

a) activating said support surface; and b) adding said oligonucleotide pools to said activated support surface to form said oligonucleotide stripes.

16. A method according to claim 15 wherein said adding is done by drawing.

17. A method according to claim 15 wherein said adding is done by piezoelectric pump.

18. A method of detecting the presence or absence of a target sequence in a sample comprising a) contacting said sample with an array according to claim 1 under conditions that permit hybridization of said target sequence, if present, to an oligonucleotide covalently attached to said array; and detecting the presence or absence of said target sequence.

19. A kit comprising an array according to claim 1 and at least one reagent.

* * * * *